(12) United States Patent
Venkatasubramanian et al.

(10) Patent No.: US 11,670,839 B2
(45) Date of Patent: ***Jun. 6, 2023

(54) ANTENNA FOR IMPLANT AND ASSOCIATED APPARATUS AND METHODS

(71) Applicant: CAMBRIDGE CONSULTANTS LIMITED, Cambridge (GB)

(72) Inventors: Arun Venkatasubramanian, Arlington, MA (US); Lonnell Leotis Ahiyya, Lowell, MA (US)

(73) Assignee: CAMBRIDGE CONSULTANTS LIMITED, Cambridge (GB)

( * ) Notice: Subject to any disclaimer, the term of this patent is extended or adjusted under 35 U.S.C. 154(b) by 510 days.

This patent is subject to a terminal disclaimer.

(21) Appl. No.: 16/809,262

(22) Filed: Mar. 4, 2020

(65) Prior Publication Data

US 2020/0235464 A1 Jul. 23, 2020

Related U.S. Application Data

(63) Continuation of application No. 15/516,549, filed as application No. PCT/GB2015/052897 on Oct. 2, 2015, now Pat. No. 10,622,707.

(Continued)

(30) Foreign Application Priority Data

Feb. 24, 2015 (GB) ...................... 1503040

(51) Int. Cl.
*H01Q 1/36* (2006.01)
*H01Q 1/27* (2006.01)
(Continued)

(52) U.S. Cl.
CPC ............. *H01Q 1/273* (2013.01); *A61N 1/375* (2013.01); *A61N 1/3758* (2013.01);
(Continued)

(58) Field of Classification Search
CPC ........ H04B 13/005; H01Q 21/00; H01Q 9/42; H01Q 7/00; H01Q 1/36; H01Q 1/27; H01Q 5/40; H01Q 1/273
See application file for complete search history.

(56) References Cited

U.S. PATENT DOCUMENTS 6,009,350 A  12/1999 Renken
6,437,750 B1  8/2002 Grimes et al.
(Continued)

FOREIGN PATENT DOCUMENTS

CA    2850445 A1   5/2013
GB    2288914 A   11/1995
(Continued)

OTHER PUBLICATIONS

Kiourti. A. et al. "Implantable and Ingestible Medical Devices with Wireless Telemetry Functionalities: a Review of Current Status and Challenges", Wiley Bioelectromagnetics, vol. 35(1): 1-15 (2014).

(Continued)

*Primary Examiner* — Graham P Smith
(74) *Attorney, Agent, or Firm* — Merchant & Gould P.C.

(57) ABSTRACT

An antenna for a medical implant device is described. The antenna has a magnetic field radiator portion and an electric field radiator portion coupled to the magnetic field radiator portion. The magnetic and electric field radiators are arranged to result in generation, by the antenna, of at least one of a transverse electric leaky wave and a transverse magnetic leaky wave in lossy body tissue of a human or animal body such that the lossy body tissue acts as a waveguide for the transverse electric leaky wave or transverse magnetic leaky wave, whereby to optimize at least one of the efficiency of the antenna and the far field gain of the antenna.

14 Claims, 12 Drawing Sheets

Related U.S. Application Data

(60) Provisional application No. 62/059,596, filed on Oct. 3, 2014.

(51) Int. Cl.
  *A61N 1/372* (2006.01)
  *H04B 13/00* (2006.01)
  *H01Q 9/42* (2006.01)
  *H01Q 5/40* (2015.01)
  *H01Q 21/00* (2006.01)
  *A61N 1/375* (2006.01)
  *H01Q 7/00* (2006.01)

(52) U.S. Cl.
  CPC .......... *A61N 1/37229* (2013.01); *H01Q 1/27* (2013.01); *H01Q 1/36* (2013.01); *H01Q 5/40* (2015.01); *H01Q 7/00* (2013.01); *H01Q 9/42* (2013.01); *H01Q 21/00* (2013.01); *H04B 13/005* (2013.01)

(56) References Cited

U.S. PATENT DOCUMENTS

| | | |
|---|---|---|
| 6,614,406 B2 | 9/2003 | Amundson et al. |
| 6,924,773 B1 | 8/2005 | Paratte |
| 7,388,550 B2 | 6/2008 | McLean |
| 8,144,065 B2 | 3/2012 | Brown |
| 8,634,928 B1 | 1/2014 | O'Driscoll et al. |
| 2009/0228074 A1 | 9/2009 | Edgell et al. |
| 2010/0015918 A1 | 1/2010 | Liu et al. |
| 2010/0149042 A1 | 6/2010 | Utsi et al. |
| 2011/0082523 A1 | 4/2011 | Nghiem et al. |
| 2013/0113666 A1 | 5/2013 | Orsi et al. |
| 2014/0002314 A1 | 1/2014 | Li et al. |

FOREIGN PATENT DOCUMENTS

| | | |
|---|---|---|
| WO | 03/044892 A1 | 5/2003 |
| WO | 2011/100618 A1 | 8/2011 |
| WO | 2015/039108 A2 | 3/2015 |

OTHER PUBLICATIONS

D. M. Grimes et al. "Minimum Q of electrically small antennas: a critical review", Microwave Optical Tech. Lett., vol. 28 (3):172-177 (2001).

M. J. Underhill et al. "Unidirectional tuned loop antennas using combined loop and dipole modes", in Proc. Inst. Elect. Eng. 8th Int, HR Radio Systems and Techniques, Conference Publication No. 474: 37-41 (2000).

D. H. Kwon "On the Radiation Q and the Gain of Crossed Electric and Magnetic Dipole Moments, IEEE", Transactions on Antennas and Propagation, vol. 53 (50): 1681-1687 (2005).

D. M. Pozar "New results for minimum Q, maximum gain, and polarization properties of electrically small arbitrary antennas", 3rd European Conference on Antennas and Propagation: 1993-1996 (2009).

A. S. Y. Poon "Electromagnetic field focusing for short-range wireless power transmission", Proc. IEEE Radio and Wireless Symposium (RWS), Santa Clara, CA (2012).

Ho, J. S. et al. "Wireless power transfer to deep-tissue microimplants", PNAS Early Edition:1-6 (2014).

S. Gabriel et al. "The Dielectric Properties of Biological Tissues: III. Parametric models for the Dielectric Spectrum of Tissues", Phys. Med. Bio.,vol. 41:2271-2293 (1996).

Orfanidis, S. J. "Electromagnetic Waves and Antennas", Online Publication (2004).

Karlsson, A. "Physical limitations of antennas in a lossy medium", IEEE Transactions on Antennas and Propagation, vol. 52: 2027-2033 (2004).

R. W. P. King et al. "Chapter 2, The Bare Antenna in Air and Dissipative Media", Antennas in Matter, Cambridge, London, U.K.: MIT Press: 138-195(1981).

Harrington, R. F. "Chapter 5, Cylindrical Wave Functions", Time Harmonic Electromagnetic Fields. New York:McGraw-Hill: 198- (1961).

G. Lovat et al, "Fundamental properties and optimization of broadside radiation from uniform leaky-wave antennas", IEEE Transactions on Antennas Propagation, vol. 54 (5):1442-1452 (2006).

A. Ip et al, "Radiation from cylindrical leaky waves", IEEE Transactions on Antennas Propagation, vol. 38 (4):482-488 (1990).

Kim, K. Y. "Guided and Leaky Modes for Circular Open Electromagnetic waveguides: Dielectric, Plasma and Metamaterial Columns", Ph.D. Thesis (2004).

Hanson, G. W. et al., "An analysis of leaky wave dispersion phenomena in the vicinity of cutoff using complex frequency plane singularities",, Radio Science, vol. 33 (4): 803-819 (1998).

T. Needham "Visual Complex Analysis", Oxford University Press (1999).

Schantz, H.G. "Near Field Phase Behavior", In proceeding of: Antennas and Propagation Society International Symposium, IEEE, vol. 3B: 134-137 (2005).

Kwon, D. H. et al. "Small Printed Ultra-Wideband Antennas Combining Electric- and Magnetic- Type Radiators".

Shulabh Gupta "Magnetoelectric Dipole Antenna Arrays", IEEE Transactions on Antennas and Propagation, vol. 62 (7):3613-3622 (2014).

International Search Report and Written Opinion for International Patent Application No. PCT/GB2015/052897, dated Jan. 14, 2016.

Search Report for British Patent Application No. GB1503040.6, dated Aug. 12, 2015.

Horizontal

Vertical

1010 = Active

1020 = Passive

ANTENNA FOR IMPLANT AND ASSOCIATED APPARATUS AND METHODS

This application is a Continuation of U.S. patent application Ser. No. 15/516,549, filed 3 Apr. 2017, which is a National Stage of PCT/GB2015/052897, filed 2 Oct. 2016, which claims benefit of British Patent Application No. 1503040.6, filed 24 Feb. 2015, and U.S. Patent Provisional Application 62/059,596, filed 3 Oct. 2014, which applications are incorporated herein by reference. To the extent appropriate, a claim of priority is made to each of the above disclosed applications.

BACKGROUND OF THE INVENTION

The present invention relates generally to antennas suitable for devices for implantation in a human or animal body and to associated apparatus and methods.

The invention has particular although not exclusive relevance to antennas used with implantable medical devices, such as but not limited to pacemakers and neurostimulation devices.

Implantable medical devices (IMDs), for human or animal bodies are now ubiquitous. Annually, more than one million pacemakers, more than two hundred thousand defibrillators, and more than one hundred and fifty thousand neurostimulation devices for pain management, epilepsy, Parkinson and many other indications are implanted each year.

Such IMDs often utilize wireless (radio frequency, 'RF') technology to enhance the versatility of implantable medical devices by allowing remote monitoring of such IMDs and the optimization of treatments using them. The integration of wireless technology with IMDs represents a significant challenge because of the substantial, inter-related and often conflicting, design constraints placed on IMDs including, for example constraints related to: size; power consumption/efficiency; reliability; durability; operating frequency; bio-compatibility; patient safety; and/or the like.

For example, whether fitted sub-cutaneously or within the peritoneal cavity, IMDs are necessarily small, to allow them to fit within the appropriate pocket in a patient's body, with sizes ranging from a few millimeters (mm) to few tens of centimeters (cm). The size of the battery generally defines the size of the IMD and hence constraints on the size of the IMD inherently limit the choice of power supply. The electronics and the battery are generally enclosed in a hermetically sealed titanium can with a Tecothane or epoxy header.

One of the main challenges facing wireless IMD design is that of antenna design, not least because the anatomical distribution of, together with the different electrical properties and configuration of, the various tissues of a human or animal body, can significantly affect the performance of the antenna. Specifically, the necessary small size of the antenna and the proximity of the antenna to lossy body tissue can result both in signal attenuation and antenna detuning by the local body tissue.

Known antennas, in devices such as pacemakers and Neurostimulation devices reside in a header of the implant. The majority of known IMD antennas are either loops or planar inverted F antennas (PIFA). Loops are current fed antennas and produce primarily a magnetic field (transverse electric (TE) mode). PIFAs, on the other hand, are quarter wavelength (or some multiple of a quarter wavelength), voltage fed, dipole antennas that generate both an electric and a magnetic field. Both these antennas have a single dominant current mode.

Power radiated by antennas is generally complex in nature having a real element and a reactive (or 'imaginary') element. The real power leaves the antenna and never returns, whereas the reactive power tends to bounce around about a fixed position (within a half wavelength called the radiansphere) of the antenna and interacts with the antenna and the surrounding environment, thereby affecting the antenna's operation. Generally, antenna design treats a human or animal body as a lossy load that detunes the antenna and therefore seeks to minimize the resonant, non-radiating reactive energy around the antenna, and keep such energy away from tissue, thereby reducing the detuning effects such that the antenna can operate at the desired frequency without the need for retuning. For higher power medical applications, such containment of the resonant energy is seen to be beneficial because it can minimize local RF heating effects that could otherwise cause bio-compatibility issues (e.g. where a local temperature increase of only a few degrees can affect the development and metabolism of cells adjacent to an implant).

SUMMARY OF THE INVENTION

The present invention seeks to provide an improved configuration for an antenna (such as a transmit antenna) of an implant and related methods and apparatus.

The present invention aims in particular to provide, but is not limited to providing, one or more of the following benefits compared to existing technology: a smaller antenna size (for similar antenna performance); an increased communication distance between the implant and the external device (especially for implant depths from 2 cm to 12 cm); a reduced sensitivity to changes in body morphology after implantation (such as a patient adding or losing weight); a lowered specific absorption rate (thereby allowing the implanted radio to transmit at higher radio power without exceeding the regulatory limits for tissue heating); and an improved radiation efficiency (and hence battery life for the implant or smaller batteries for a specified implant life span). Still other objects and advantages of the invention will be apparent from the detailed description and the drawings.

In one aspect of the invention there is provided an antenna for an implant device for implant in a human or animal body, the antenna comprising: a magnetic field radiator portion; and an electric field radiator portion coupled to the magnetic field radiator portion at a predetermined location on the magnetic field radiator portion; wherein said predetermined location on the magnetic field radiator portion is predetermined to be a location that results in generation, by the antenna, of at least one of a transverse electric leaky wave and a transverse magnetic leaky wave in lossy body tissue of said human or animal body such that said lossy body tissue acts as a waveguide for said at least one of a transverse electric leaky wave and a transverse magnetic leaky wave, whereby to optimize at least one of the efficiency of the antenna and the far field gain of the antenna.

The magnetic field radiator may comprise a loop, formed by a first conducting member, having a feed pin at one end and a ground point at the other. The magnetic field radiator may be configured to generate a magnetic field in a frequency of interest as current flows from the feed pin to the ground point. The magnetic field radiator may be configured to generate a transverse electric leaky wave in a frequency of interest in said lossy body tissue.

The electric field radiator may be formed by a second conducting member that is connected to the first conducting member at said predetermined location. The electric field radiator may be connected to said magnetic field radiator at a specific location on the perimeter of the loop for example to minimize the current reflected back into the loop and disrupting the magnetic current flowing through the loop whereby to reduce a phase difference between the electric and the magnetic fields generated in the lossy body tissue.

The antenna may further comprise a third conducting member capacitively coupled to a perimeter of the first conducting member whereby to reduce a phase difference between the electric and the magnetic fields. The third conducting member may be connected to the perimeter of the loop such that the second and third conducting members are appropriately located so as to generate multiple modes of transverse electric and transverse magnetic leaky waves.

The antenna may further comprise a housing for housing the magnetic field radiator portion and electric field radiator portion wherein said ground point may be a pin connected to a ground potential on said housing. The antenna may further comprise a circuit board comprising circuitry for controlling operation of said implant device wherein said ground point may be a pin connected to a ground potential on said circuit board.

The antenna may be formed by at least one of laser cutting, stamping of a metal material, and direct structuring (e.g. laser direct structuring (LDS)) on a dielectric member. The antenna may further comprise an implant header, wherein said antenna may be formed by direct structuring on a dielectric member of said implant header.

The antenna may be formed by of at least one of titanium, copper, platinum and iridium.

The magnetic loop may comprise a capacitive gap configured to reduce a resonant frequency of the loop. A third conducting member may extend close to the capacitive gap, wherein the conducting member may have a length configured such that an input impedance of said loop matches an impedance of a radio chipset.

The antenna may be configured such that, when implanted, the body tissue enhances the efficiency of the antenna. The antenna may be configured such that, when implanted, the body tissue enlarges the effective aperture of the antenna.

In one aspect of the invention there is provided an implant device comprising a transmitter provided with an antenna as recited above.

The feed pin of the antenna may be connected, on one end to the antenna in a header of the implant device and one end may be connected to a matching circuit for matching an impedance of the antenna to a transmitter output. The matching circuit may be electrically tunable.

In one aspect of the invention there is provided a method of designing an antenna, for an implant device for implant in a human or animal body, the method comprising: generating an initial design, for use as a current design of said antenna, targeted at achieving at least one predetermined design goal; generating a body model for modelling lossy body tissue of said human or animal body; simulating performance of an antenna formed in accordance with said current design, and located within a body corresponding to said body model; comparing simulated performance of said antenna with said at least one predetermined design goal to determine if said current design meets said at least one predetermined design goal; modifying said current design when the current design does not meet said at least one predetermined design goal, and repeating said simulating and said comparing for said current design so modified; and confirming said current design as the basis for fabrication of an antenna when the current design meets said at least one predetermined design goal; wherein said confirming confirms a current design as the basis for fabrication that is configured to result in an antenna that generates, when in operation and located in said human or animal body, of at least one of a transverse electric leaky wave and a transverse magnetic leaky wave in lossy body tissue of said human or animal body such that said lossy body tissue acts as a waveguide for said at least one of a transverse electric leaky wave and a transverse magnetic leaky wave.

In one aspect of the invention there is provided a method of fabricating an antenna for an implant device for implant in a human or animal body, the method comprising: generating a design as the basis for fabrication of said antenna using the method recited above; fabricating said antenna to said design.

In one aspect of the invention there is provided an antenna for an implant device for implant in a human or animal body, fabricated using the above method.

In one aspect of the invention there is provided a method of transmitting a radio signal from an implant device, the method comprising: locating said implant device in a human or animal body; generating, at a transmitter of said implant device, said radio signal; generating, at an antenna of said transmitter, at least one of a transverse electric leaky wave and a transverse magnetic leaky wave, corresponding to said radio signal, in lossy body tissue of said human or animal body; and using said lossy body tissue as an effective waveguide for said at least one of a transverse electric leaky wave and a transverse magnetic leaky wave, whereby to optimize at least one of the efficiency of the antenna and the far field gain of the antenna.

Aspects of the invention extend to computer program products such as computer readable storage media having instructions stored thereon which are operable to program a programmable processor to carry out a method as described in the aspects and possibilities set out above or recited in the claims and/or to program a suitably adapted computer to provide the apparatus recited in any of the claims.

Each feature disclosed in this specification (which term includes the claims) and/or shown in the drawings may be incorporated in the invention independently (or in combination with) any other disclosed and/or illustrated features. In particular but without limitation the features of any of the claims dependent from a particular independent claim may be introduced into that independent claim in any combination or individually.

BRIEF DESCRIPTION OF THE DRAWINGS

Embodiments of the invention will now be described by way of example only with reference to the attached figures in which.

DETAILED DESCRIPTION OF THE PREFERRED EMBODIMENT(S)

Figure 1:
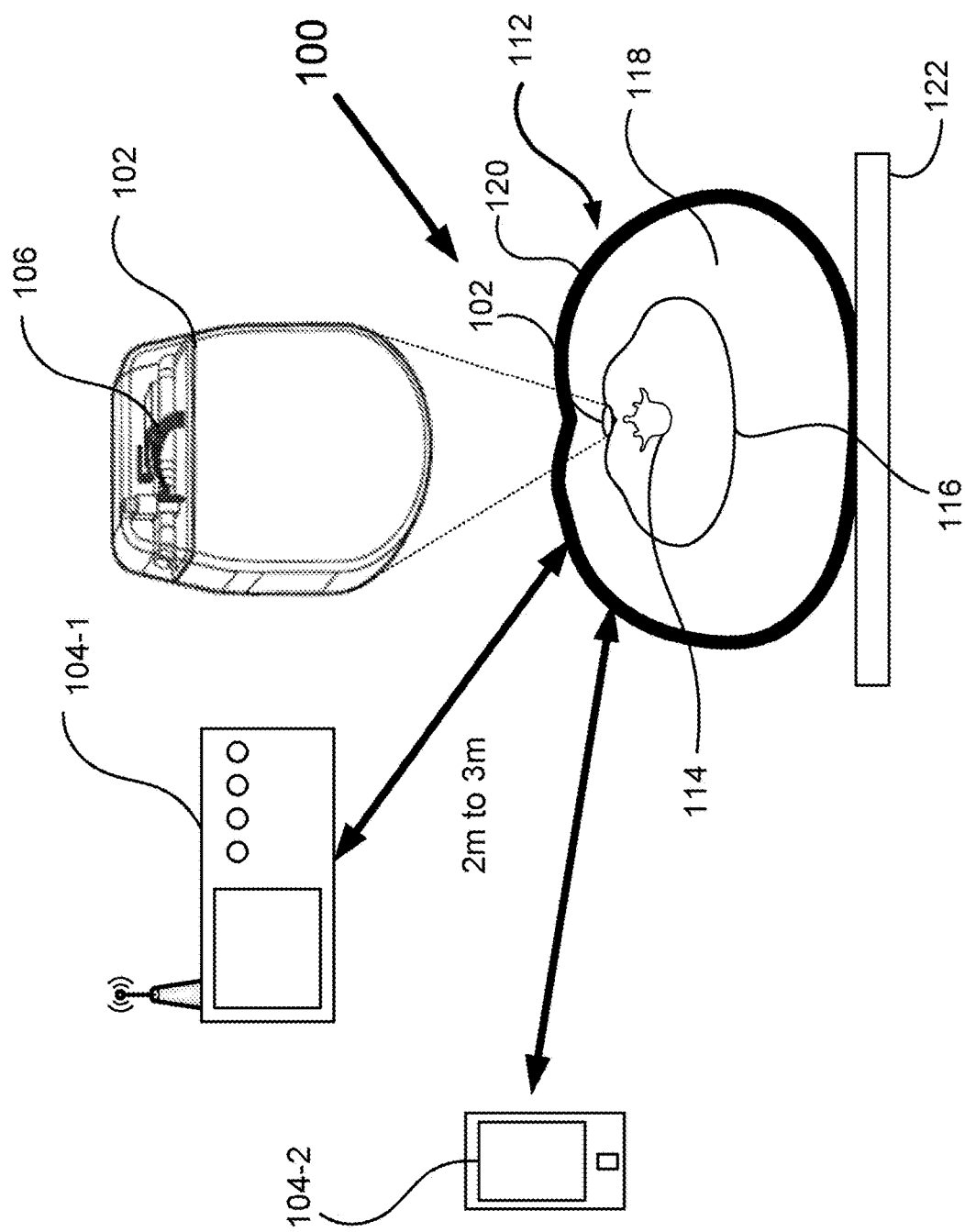
FIG. 1 illustrates, in simplified overview, a medical implant system.

FIG. 1 shows, in simplified overview, a medical implant system generally at 100. The implant system comprises an implant device 102 comprising a transmitter for transmitting radio frequency signals, and an associated fixed or mobile (e.g. tablet) based programmer 104-1, 104-2 comprising a receiver for receiving signals transmitted from the implant device to allow the programmer 104 to monitor the implant device 102 when the implant device 102 is implanted in a patient and operational.

The implant device 102 comprises an implant can which encloses the analog circuitry, radio circuitry and battery of the device. The radio circuitry of the implant device 102 is configured to transmit signals in one of the industrial, scientific and medical (ISM) portions of the radio spectrum or any other suitable part of the spectrum. In the example shown in FIG. 1 the transmitter is configured to transmit signals in a 2.4 GHz to 2.5 GHz ISM frequency band centered on 2.45 GHz (suitable for Bluetooth communication). It will be appreciated, however, that in other examples the transmitter may be configured for transmission in one or more other frequency bands depending, for example, on local preferences or regulatory requirements (e.g. in the Medical Implant Communication Service (MICS) band between 402 and 405 MHz). To facilitate transmission in the appropriate radio band, the transmitter of the implant device 102 is provided with an appropriately configured antenna 106 via which to transmit signals for receipt by the receiver of the programmer 104.

In FIG. 1, the implant device is shown implanted inside the body 112 of a patient (shown in simplified transverse cross-section) lying prone on an operating table 122 or the like. In this example, the implant is located in the buttocks area (typically just below the belt line) of a patient with a large waist (e.g. ≡60 inch). The patient's body 112 comprises many different types of tissue including the vertebrae 114 (i.e. the backbone region) surrounded by predominantly muscle region 116, which in turn is surrounded by a fat layer 118 and an external skin layer 120.

In this example, the programmer 104 is located at some distance (typically 2 m to 3 m) from the patient, effectively in the far field of (ten wavelengths or greater from) the transmitter of the implant device 102. By way of example, at 2.45 GHz, the free space wavelength is approximately 12.5 cm (compared to a guided wavelength in the region of 1.7 cm in muscle). Accordingly, when the implant is a pacemaker, or the like, implanted approximately 8 cm beneath the skin, the pacemaker will be around 25 wavelengths away from the receiver in the programmer 104 (which is firmly in the far field).

As explained in more detail later, there are significant differences between the dielectric constant and conductivity (or loss tangent) of fat (e.g. in terms of water content) in comparison to skin and muscle for the frequency bands of interest (e.g. both the 2.4 GHz to 2.5 GHz Bluetooth band or the 402 to 405 MHz MICS band). This leads to two key propagation mechanisms as shown in FIG. 2 which illustrates, in simplified form, key electromagnetic wave propagation mechanisms in a human body for radio frequency signals from an implant device such as that illustrated in FIG. 1.

Figure 2:
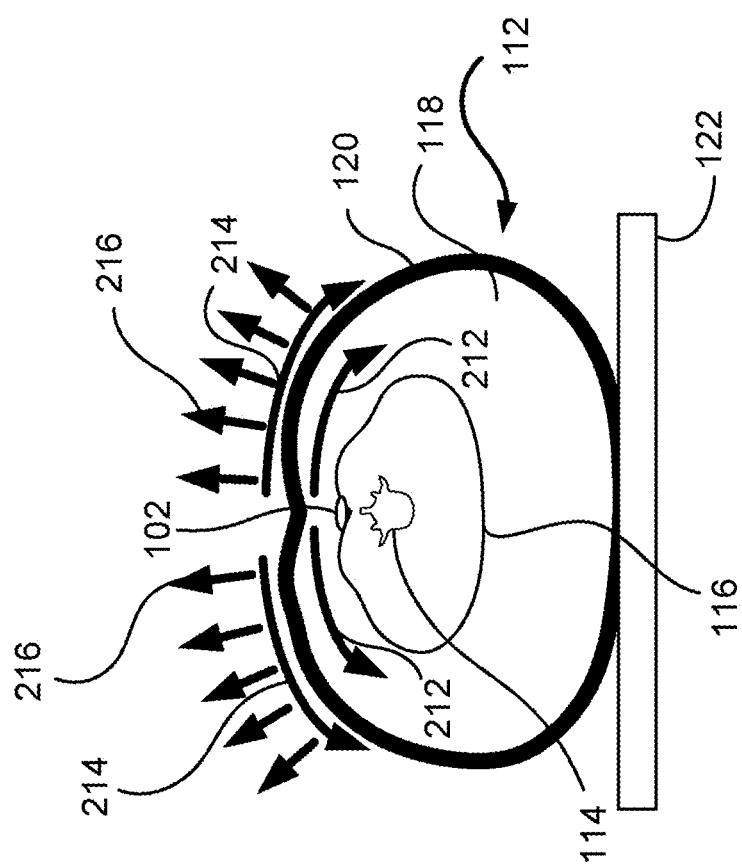
FIG. 2 illustrates, in simplified form, key electromagnetic wave propagation mechanisms in a human body.

As seen in FIG. 2, in a first propagation mechanism 212 comprises guided and leaky wave propagation in the fat layer 118 and a second propagation mechanism 214 comprises surface wave propagation on the skin layer. In more detail, electromagnetic waves propagating from the fat layer to the skin layer or from the fat layer to the muscle layer propagate from a rarer (lower dielectric constant) to a denser (higher dielectric constant) medium resulting in a portion of the energy being reflected back into (and then around) the fat layer and a portion of energy transmitted into the skin or muscle layer. In known implant technology, this can significantly inhibit (or even prevent) electromagnetic waves from leaving the body as shown at 216.

Beneficially, the antenna 106 of this example is an implantable compound antenna has a combination of a loop and a monopole configured such that the gain of the antenna is increased by approximately 4 dB compared to a standard loop antenna. The implantable antenna 106 is designed using a particularly advantageous method in which the antenna design is specifically tailored to enhance the far field gain of the transmitter, using a model of the patient's body, to take advantage of the electromagnetic nature of the human body and, in particular, to make use of, rather than suppress, the effects of the propagation mechanisms exhibited in the body. Specifically, the implantable compound antenna 106 is designed using a new method that has the potential to allow the successful use of compound antennas, that are immersed in dispersive lossy media such as human body tissue, for effective communication with external transceivers that are located at a significantly greater distance, compared to that of known implant communication technologies, from the transmitter (in the far-field). In operation, the antenna 106 excites electric and magnetic fields in lossy dielectric media (like muscle and fat) such that they achieve enhanced radiation efficiency compared to standard dipole antennas or loop antennas.

In effect, the method results in an antenna design that makes use of the body tissue, as a lossy dielectric waveguide, to excite leaky wave modes in the fat and skin layer, such that the energy radiated by the implant antenna is not trapped inside the body but instead couples efficiently to the air medium surrounding the body, so as to achieve enhanced radiation efficiency.

This contrasts with more conventional implant antenna design in which the feed point impedance of the antenna is merely tuned to match the antenna's impedance to the impedance of the transceiver by either measuring power locally at the implant or by using closed loop control with the external device. Whilst this may involve measuring the loading of the body tissue on the implant antenna it does not use the body tissue to enhance radiation efficiency.

The antenna 106 of FIG. 1, the method of designing it, and the other examples described herein, have the potential to provide one or more of the following advantages: a smaller antenna size; a maximized communication distance between the implant and the external device for implant depths from 2 cm to 12 cm; reduced sensitivity to changes in body morphology after implantation (patient adding or losing weight), lowered specific absorption rate (permits the implant radio to transmit at higher radio power without exceeding the regulatory limits for tissue heating) and an improved battery life of the implant or smaller batteries for fixed implant life span.

It will be appreciated that, whilst the techniques described herein are particularly beneficial for the design of compound antennas, the methodology can be beneficially extended such that any antenna type can be designed to excite leaky wave modes in the different body tissue thereby effectively increasing the aperture of the antenna to enhance the antenna's radiation efficiency.

Radio Propagation in the Human Body

Whilst those skilled in the art will be familiar with radio propagation mechanisms in the human body a brief summary of the science of such mechanisms, and how it is beneficially applied in the technology disclosed herein, will now be provided, by way of example only, to aid understanding.

Radio wave propagation in the human body is quite involved as the body is a dispersive lossy dielectric medium with a complex dielectric constant $\epsilon_r$ given by the so called 4 pole Cole-Cole model:

$$\epsilon_r(\omega) = \epsilon_\infty + \sum_{n=1}^{4} \frac{\Delta\epsilon_n}{1 + (j\omega\tau_n)(1-\alpha_n)} + \frac{\sigma_i}{j\omega\epsilon_0} \quad (1)$$

where $\omega$ is the angular frequency for the radio wave, $\epsilon_\infty$ is the permittivity at high frequencies (in the THz frequency range with $\omega\tau_n \gg 1$), $\epsilon_0$ is the permittivity of free space, $\sigma_i$ is the ionic conductivity for each dispersion region, $\tau_n$ is the relaxation time, $\alpha_n$ is a distribution parameter which causes a broadening of the dispersion (0 for water, >0 for most tissues, negligible for body fluids), and $\Delta\epsilon_n$ the difference between the low frequency permittivity $\epsilon_s$ ($\omega\tau_n \ll 1$) and the high frequency permittivity.

The values of these variables for different types of tissue are given in [17].

Figure 3:
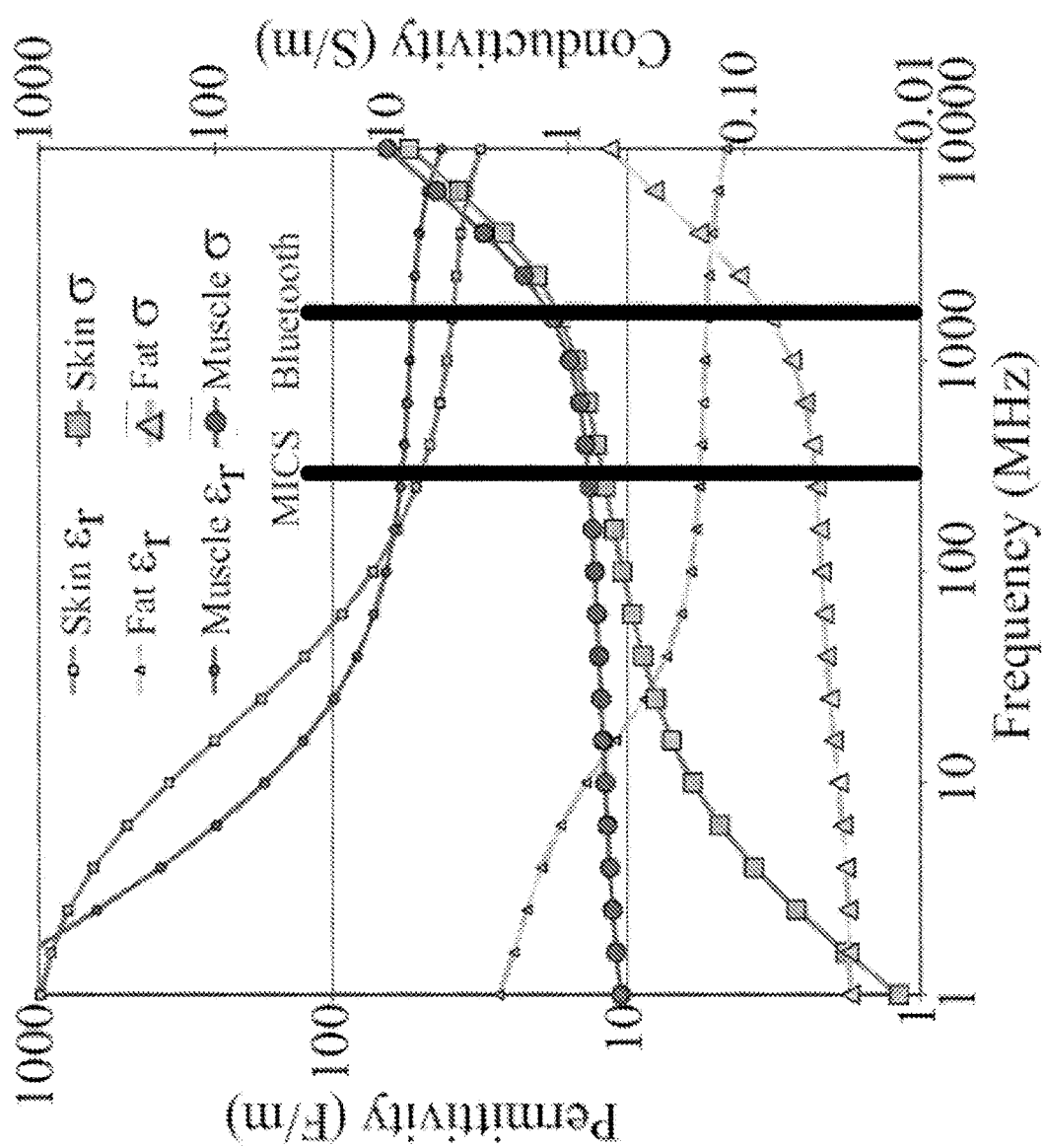
FIG. 3 is a plot of the typical dielectric constant and the conductivity for skin, fat, and muscle.

FIG. 3 shows a plot of the dielectric constant (in Farads/meter) and the conductivity (in Siemens/meter) for skin, fat, and muscle. FIG. 3 illustrates the significant difference in the dielectric constant and conductivity (or loss tangent) of fat in comparison to skin and muscle, both in the 402 and 405 MHz MICS band and the 2.4 to 2.5 GHz Bluetooth band. Specifically, both skin and muscle can be seen to exhibit similar dielectric constants, for these frequency bands, generally in the 50 F/m to 70 F/m range. Contrastingly fat can be seen to have a much lower dielectric constant in the 5 to 10 F/m region. This leads to the two key propagation mechanisms described above with reference to FIG. 2, namely: (1) guided and leaky wave propagation in the fat layer, and (2) surface wave propagation on the skin layer.

As explained above, therefore, electromagnetic waves propagating from the fat layer to the skin layer or from the fat layer to the muscle layer always propagate from a rarer (lower dielectric constant) to a denser (higher dielectric constant) medium resulting in a portion of the energy being reflected into the fat layer and a portion of energy transmitted into the skin or muscle layer. The ratio of the reflected and the transmitted portions depends on the electrical properties of the tissue, the polarization of the electromagnetic wave, and the angle of incidence of the wave at either interface. The energy transmitted into the muscle layer is lost as heat but the energy transmitted in the skin layer is important, in the examples disclosed herein, because it maximizes the coupling of energy out of the body.

The wave number, k, in units of $m^{-1}$, of the electromagnetic wave is complex and is given as:

$$\vec{k} = \vec{\beta} - j\vec{\alpha} \quad (2)$$

where $\vec{\beta}$ is the propagation constant (in radians/meter) that provides information about the direction of propagation of the amplitude of the electromagnetic wave, and $\vec{\alpha}$ is the attenuation constant (in Neper/meter) that provides information about the direction of propagation of the amplitude wavefronts of the electromagnetic wave. Based on the amplitude and phase of these quantities there can exist different types of complex waves in different body tissue.

Figure 4:
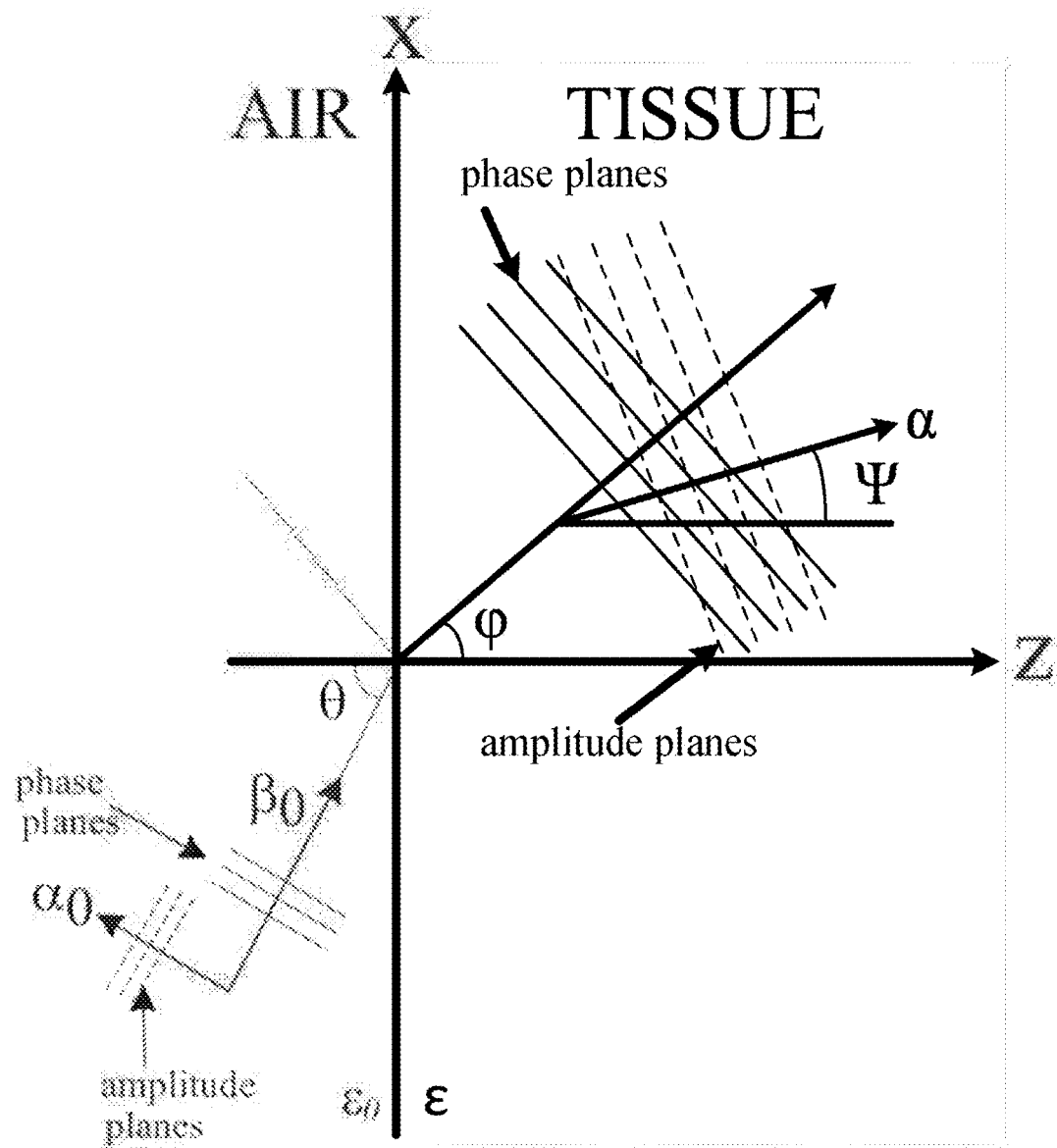
FIG. 4 illustrates constant planes of amplitude and phase of a propagating wave in body tissue and air.

Referring to FIG. 4, this illustrates the constant planes of amplitude and phase of the propagating wave in a dispersive medium. The angle $\phi = \arctan(\beta_{0x}/\beta_z)$ is the transmitted wave angle and $\psi = \arctan(\alpha_{0x}/\alpha_z)$ is the angle of the normal vector to the amplitude planes from the normal to the interface plane (z-axis in FIG. 3).

A dispersion diagram relates the values of $\alpha$ and $\beta$, as per (2), as functions of frequency. The method to obtain the dispersion diagram is by solving for the zeros of the related characteristic equation whilst varying the frequency f. The characteristic equation for axially symmetric wave modes is given by:

$$\frac{\varepsilon_{r1}}{k_1}\frac{J_1(k_1\rho)}{J_0(k_1\rho)} - \frac{\varepsilon_{r2}}{k_2}\frac{H_1^{(2)}(k_2\rho)}{H_0^{(2)}(k_2\rho)} = 0 \text{ for } TM_{0n} \quad (3)$$

$$\frac{\mu_{r1}}{k_1}\frac{J_1(k_1\rho)}{J_0(k_1\rho)} - \frac{\mu_{r2}}{k_2}\frac{H_1^{(2)}(k_2\rho)}{H_0^{(2)}(k_2\rho)} = 0 \text{ for } TE_{0n}$$

where $\mu$ is the magnetic permeability, $\varepsilon$ is the electric permittivity, $H_n^{(2)}$ is the Hankel function of the second kind of order n, $J_n$ is the Bessel function of the first kind of order n, $\rho$ is the radius of the dielectric medium and $k_1$ and $k_2$ are given by:

$$k_1 = k_0\sqrt{\epsilon_1\mu_1 - z^2} \quad (4)$$

$$k_2 = k_0\sqrt{\epsilon_2\mu_2 - z^2} \quad (5)$$

The Davidenko method is used to calculate the roots of (3) as given in [25].

Figure 5:
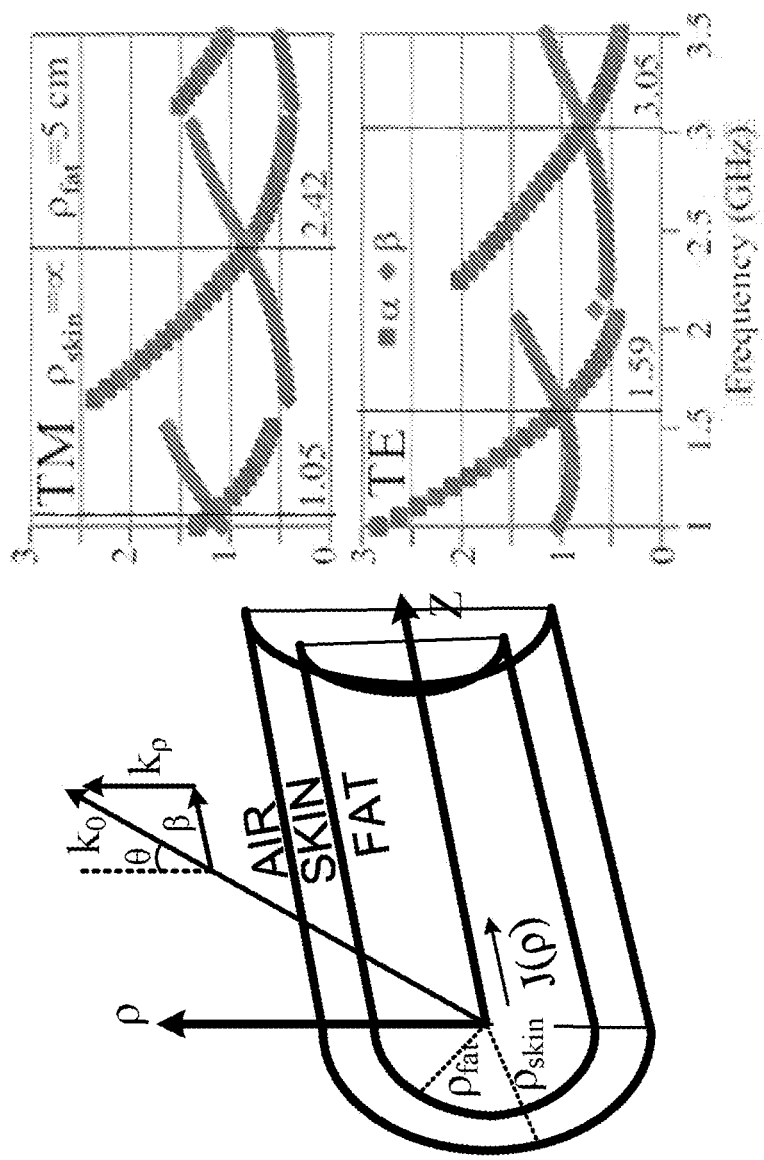
FIG. 5 is a dispersion diagram for real and imaginary parts of a complex wave number in a cylindrical body model for fat and skin tissue.

FIG. 5 shows a dispersion diagram for the real and imaginary parts of a complex wave number in a cylindrical body model with fat and skin tissue. The plot assumes a fat layer of radius 5 cm. The skin layer is assumed to be infinite homogenous lossy medium. This plot provides information regarding the type of wave modes that can be excited in different body tissue. The plot shows the following interesting features:

1. The $\vec{\beta}$ in the fat layer is always less than $|\vec{k}|$ in the skin layer indicating that the phase velocity of the wave propagating in the fat layer is faster than the speed of light. This permits the existence of leaky wave modes that can contribute to radiation.
2. There are specific frequencies for the transverse electric (TE) and transverse magnetic (TM) modes where the real and imaginary parts of the complex wavenumber are equal i.e. $\vec{\alpha} = \vec{\beta}$ known as the 'resonance gain condition'. This condition permits maximum radiation to leak out of a lossy dielectric waveguide when there is a radiating current element $\vec{J(\rho)}$ oriented along the axis of the cylinder. The specific frequencies where the $\vec{\alpha} = \vec{\beta}$ condition holds are different for TE and TM polarization suggesting that using compound antennas would enable leaky modes to be generated in different frequency bands.

Body morphology varies from one patient to the next and following implantation as a patient gains or loses weight and muscle mass. This results in differences in the electromagnetic environment surrounding the implant antenna. This confirms that the implant antenna designs proposed need to be robust enough to maintain performance for different body types.

Figure 6:
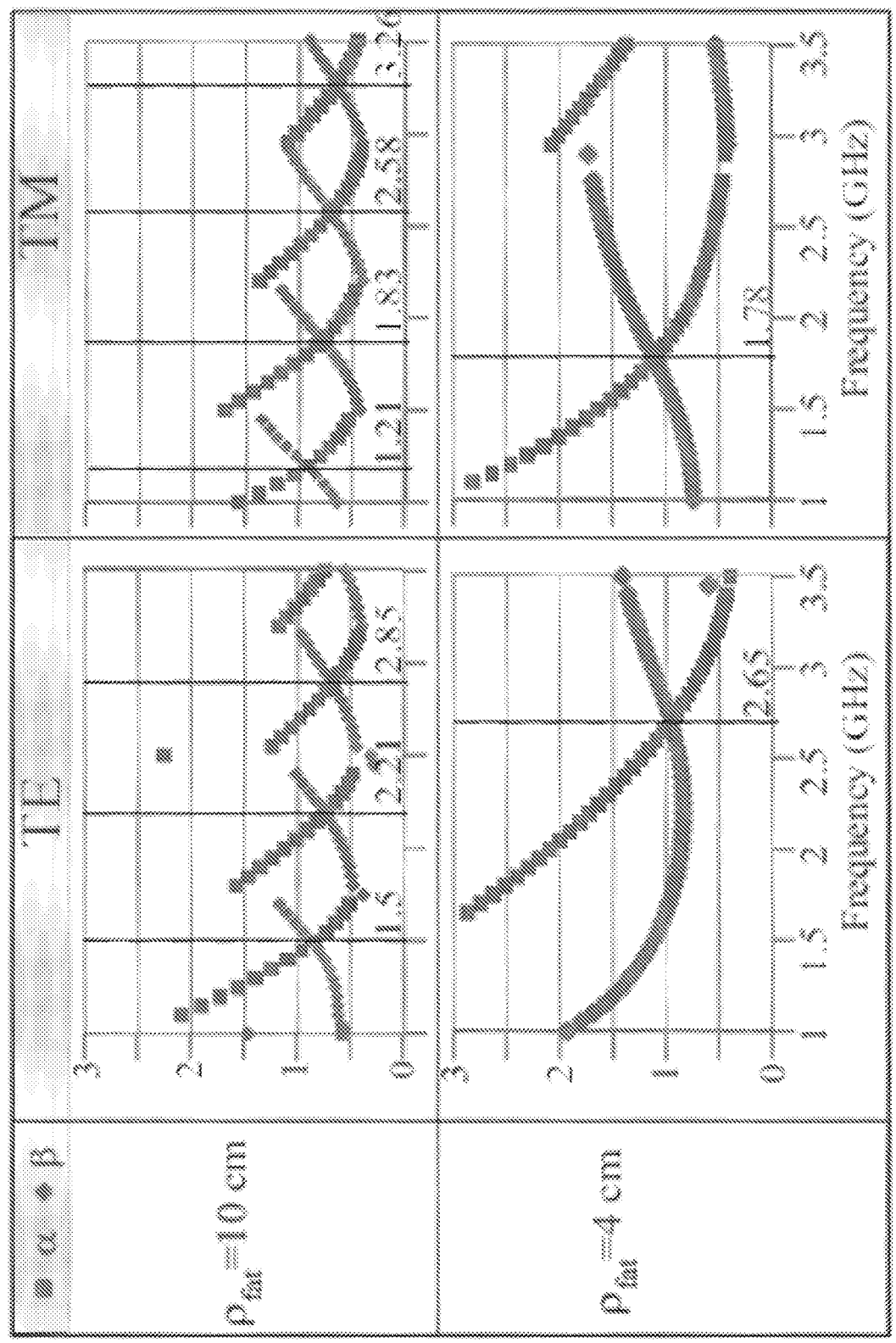
FIG. 6 shows Transverse Electric (TE) and Transverse Magnetic (TM) dispersion diagrams for different thicknesses of fat.

FIG. 6 shows the transverse electric (TE) and transverse magnetic (TM) dispersion diagram for 8 cm of fat and 20 cm of fat respectively ($\rho_{fat}$=4 cm and $\rho_{fat}$=10 cm respectively). FIG. 6 shows that the number of resonant frequencies where $\vec{\alpha} = \vec{\beta}$ move depending on the thickness of the fat layer and whether the antenna is TE or TM. This suggests that having a compound field antenna that generates at least one TM and one TE mode wave orthogonal to each other implies that one of the two polarizations will excite leaky wave modes with maximum radiation efficiency present in the frequency band of interest.

Based on the above observations of wave dispersion in body tissue a novel method has been developed for designing compound field antennas that exhibit such orthogonality of the TE and the TM polarization and in which leaky wave modes are generated, when the antennas are in operation, so as to enhance radiation efficiency.

Considering first a implantable compound antenna comprising a dipole (TM) and a loop (TE) antenna inside a dispersive medium like the body tissue in which: (a) the loop antenna has an area A (in mm$^2$) and a current $I_M$ (in mA) flowing through it; and (b) the dipole antenna has a length L and current $I_E$; the phase of the electric and magnetic fields of a dipole and a loop inside the body tissue is given by:

Magnetic Loop $$\phi_E = kr - \arctan(kr) + \frac{\pi}{2}$$

$$\phi_H = kr - \arctan\left(\frac{kr}{1-(kr)^2}\right)$$

Electric Dipole $$\phi_E = kr - \arctan\left(\frac{kr}{1-(kr)^2}\right) + \frac{\pi}{2}$$

$$\phi_H = kr - \arctan(kr)$$

where the wave number k is given by equation (2) and r is the radial distance from the antenna. The phase difference between the two fields $\Delta$ is given by:

$$\Delta = \frac{\pi}{2} + (-1)^p \arctan((kr)^3) \tag{6}$$

where p=1 for electric dipole (TM polarization) and 2 for magnetic dipole (TE polarization). The impedance of the dipole and loop normalized to the free space impedance of 120π Ω is given as:

$$\hat{Z}_E = \frac{(kr)^2}{1+(kr)^2} + j\frac{-1}{(kr)(1+(kr)^2)} \tag{7}$$

$$\hat{Z}_H = \frac{(kr)^4}{(kr)^4-(kr)^2+1} + j\frac{kr}{(kr)^4-(kr)^2+1} \tag{8}$$

These equations suggest that very close to the antenna a small electric dipole appears like a high impedance capacitive open circuit and a small magnetic loop looks like a low impedance short circuit. The loop antenna has a magnetic dipole moment $\vec{p}_m$ and the dipole antenna has an electric dipole moment $\vec{p}_e$ which are related as follows:

$$\vec{p}_m = A \exp^{jB} Z \vec{p}_e \tag{9}$$

where $Z = \sqrt{\frac{\mu}{\epsilon_r(\omega)}}$ is the impedance of the dispersive medium, A is the amplitude ratio and B is the phase difference between the electric and magnetic dipole moments. B is related to the complex wave number of the medium as follows:

$$\cos(B) = \frac{(kr)^3}{\sqrt{1+(kr)^6}} \tag{10}$$

The radiation efficiency of an antenna embedded in a dispersive medium is given by:

$$\eta_{eff} = \begin{cases} -\dfrac{\mathrm{Re}[Z]}{\mathrm{Re}[j|k]^2 a^2 Z H_l(ka)\left((H_l)'(ka)+\dfrac{H_l(ka)}{ka}\right)^*} & \text{magnetic antenna} \\ -\dfrac{\mathrm{Re}[Z]}{\mathrm{Re}[j|k]^2 a^2 Z H_l^*(ka)\left(H_l'(ka)+\dfrac{H_l(ka)}{ka}\right)} & \text{electric antenna} \end{cases} \tag{11}$$

where a is the radius of the smallest sphere that completely encloses the implant antenna, $H_l$(ka) is the spherical Hankel function of the second kind with an order l. Physically l stands for the number of modes that the electric or magnetic current on the antenna will support and contribute to radiation.

Implant having Single Band Antenna

FIGS. 7(a) and 7(b) illustrate the implant device 102 of FIG. 1 in more detail.

Figure 7:
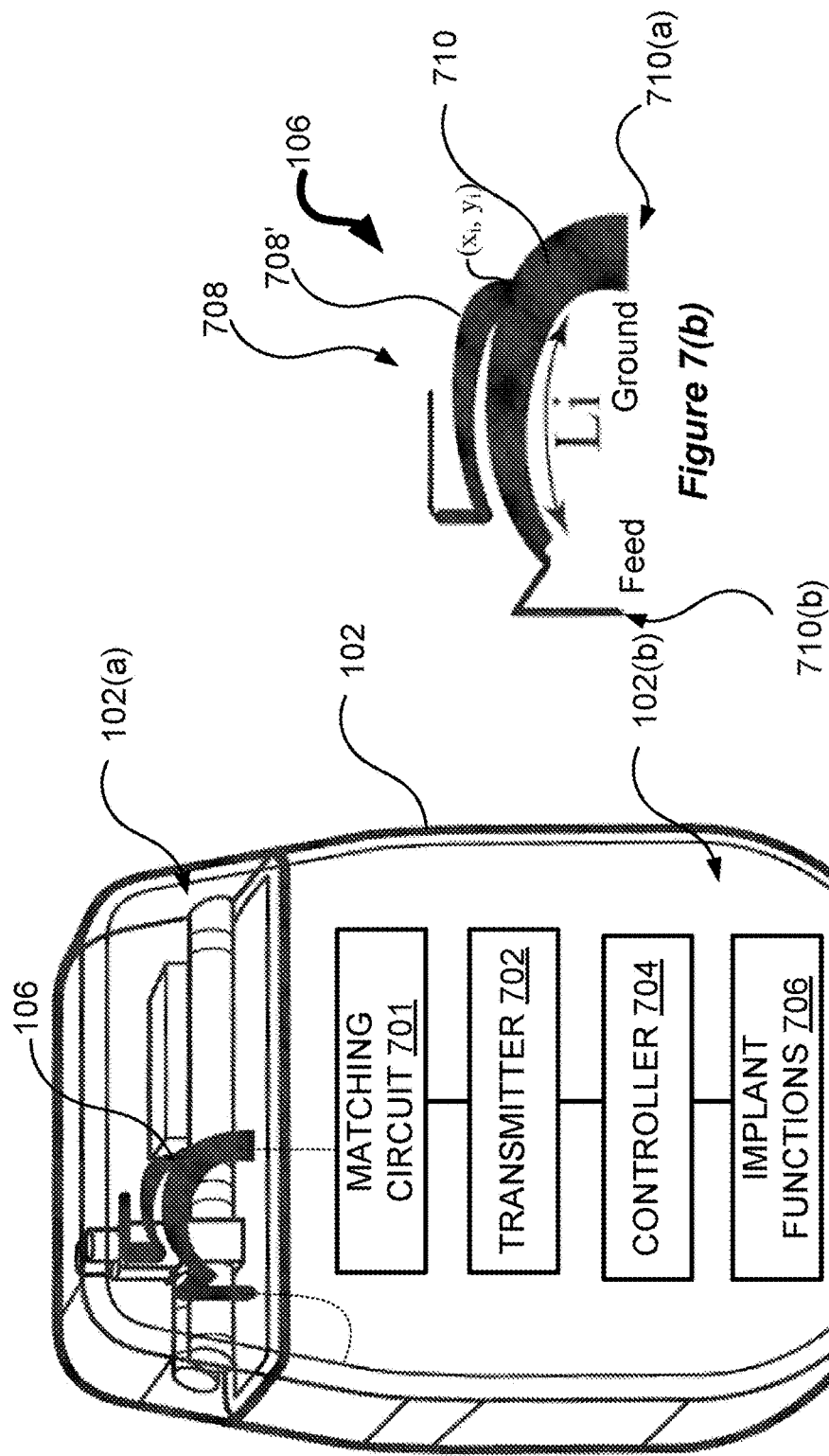
FIGS. 7(a) and 7(b) illustrate an implant device suitable for the medical implant system of FIG. 1.

As seen in FIG. 7, the implant device 102 comprises a housing (or 'can') having a header portion 102(a) and a body portion 102(b).

The header portion 702(a) is fabricated from a suitable material such as, for example, a combination of tecothane and medical grade epoxy which has a relative dielectric constant of 3 to 5 F/m. The header portion comprises the antenna 106 while the body portion 102(b) houses, amongst other things, the antenna 106, a matching circuit 701, a transmitter 702, a controller 704 and one or more implant functions 706.

The matching circuit 701 is electrically tunable to allow appropriate matching of the impedance of the antenna 106 to the transmitter 702 output. The transmitter 702 operates under the control of the controller 704 which also controls general operation of the IMD's implant functions 706 (e.g. its operation as a pacemaker, defibrillator, neurostimulator or the like).

The antenna 106 is shown in more detail in FIG. 7(*b*). The antenna 106 can be manufactured using any suitable materials using any appropriate manufacturing technology. For example, the antenna 106 may be formed by laser cutting or stamping and may be fabricated from suitable metal, such as titanium, copper or platinum iridium, commonly used in medical implants. In a particularly advantageous example, the antenna is formed by laser direct structuring of an appropriate antenna material in a dielectric member in the header portion 102(*a*).

The antenna 106 comprises a single dipole-loop pair where the dipole moments are fed in phase quadrature. The antenna 106 is configured for single band operation in the Bluetooth band (in the 2400 to 2480 MHz band) and comprises a compound antenna having a magnetic field radiator portion 710 and an electric field radiator portion 708.

The magnetic field radiator portion 710 is the transverse electric (TE) component of the compound antenna 106 and is formed by a conducting member forming a 'loop' that is generally curved in shape. The loop 710 has two ends 710(*a*) and 710(*b*) arranged to form a generally open base portion that may be connected via appropriate circuitry to the transmitter 702. One end of the loop is a feed point 710(*b*) that is typically connected to a feed pin, or the like, whilst the other end provides a ground connection that is connected to a ground point 710(*a*). The magnetic field radiator portion 710 has a shape configured to generate a transverse electric leaky wave in a frequency of interest, in the lossy body tissue of the implant patient, as the current flows from the feed pin to the ground point. The ground connection may be provided via a pin connected to a ground potential on a circuit board inside the housing, or the entire housing could form the ground plane.

The electric field radiator 708 is the transverse magnetic (TM) component of the compound antenna 106 and is formed by a curved or meandered conducting member that is located externally to the loop 710. The electric field radiator 708 comprises a stub portion 708' coupled to the loop portion 710 at a connection point $(x_i, y_i)$ on the perimeter of the loop that is specifically designed to cause the magnetic current flowing through the loop 710 and incident on the electric field radiator 708 to be reflected such that the reflection current amplitude is minimized and does not disrupt the magnetic current flowing in the loop 710 thereby resulting in a minimization of the phase difference between the electric and the magnetic fields generated in the lossy body tissue. Thus, the electric field radiator portion 708 is configured to generate a transverse electric and a transverse magnetic leaky wave, in a frequency of interest, in the lossy body tissue of the implant patient, thereby increasing the efficiency of the antenna structure.

The antenna 106 is thus configured, in accordance with the principles described herein, to provide orthogonality of the of the TE and the TM polarization, to excite leaky wave modes in the fat and skin layer in operation, and to maximise far field gain of the transmitter. Specifically, the antenna 106 has a geometry in which connection point $(x_i, y_i)$ of the stub along the perimeter of the loop portion 710 and the length of the stub $L_i$ is configured to tune the antenna to provide the desired orthogonality, leaky wave modes and far field gain.

Implant having Dual Band Antenna

Figure 8:
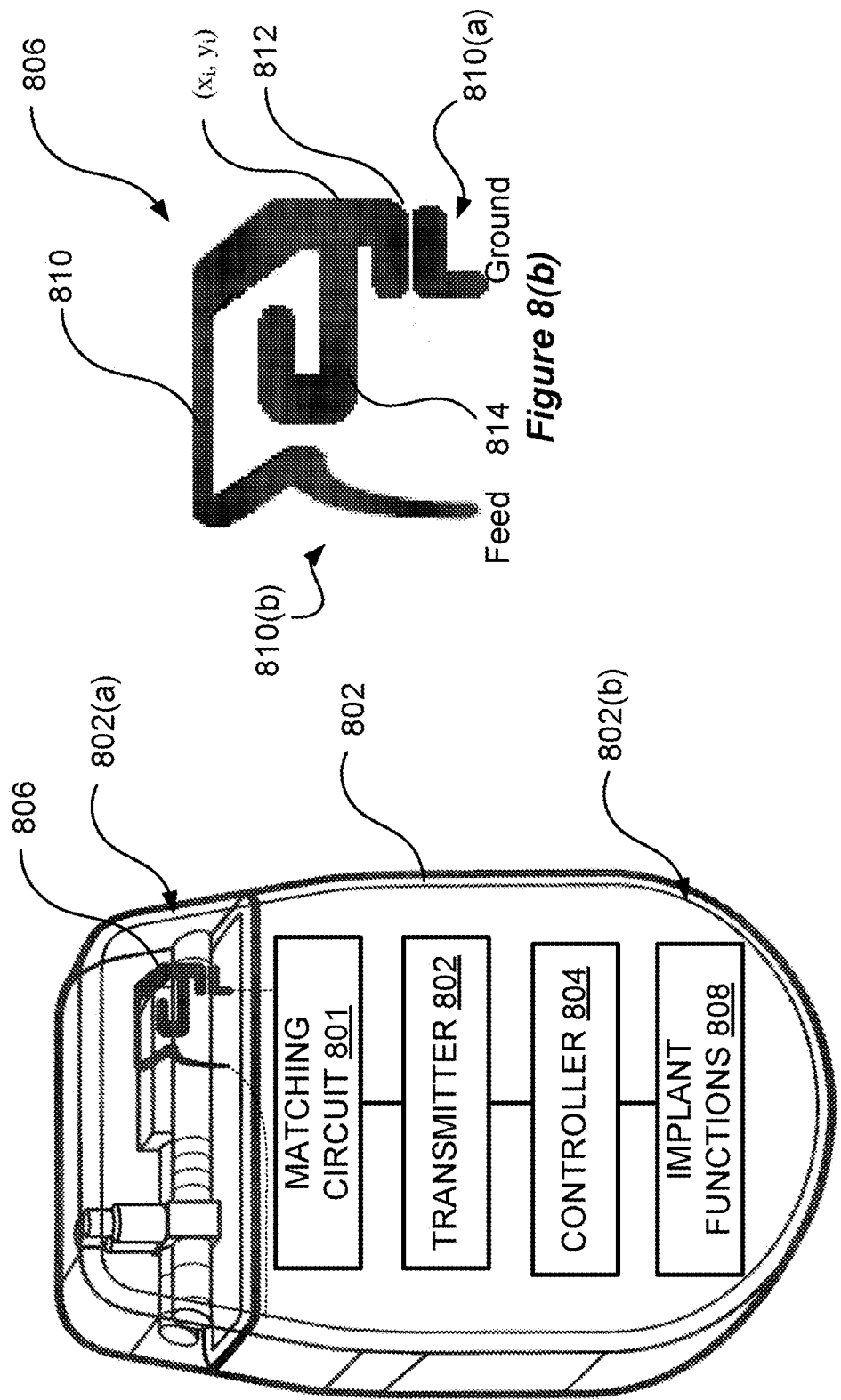
FIGS. 8(a) and 8(b) illustrate another implant device suitable for the medical implant system of FIG. 1.

FIGS. 8(*a*) and 8(*b*) illustrate another implant device 802 similar to that shown in FIG. 1.

As seen in FIG. 8, like the device 102 of FIG. 7, the implant device 802 comprises a housing (or 'can') having a header portion 802(*a*) and a body portion 802(*b*).

The header portion 802(*a*) is fabricated from a suitable material such as, for example, a combination of tecothane and medical grade epoxy which has a relative dielectric constant of 3 to 5 F/m. The header portion 802(*a*) comprises an antenna 806 while the body portion 802(*b*) houses, amongst other things, the antenna 806, a matching circuit 801, a transmitter 802, a controller 804 and one or more implant functions 808.

The matching circuit 801 is electrically tunable to allow appropriate matching of the impedance of the antenna 806 to the transmitter 802 output. The transmitter 802 operates under the control of the controller 804 which also controls general operation of the implant device's implant functions 808 (e.g. its operation as a pacemaker, defibrillator, neurostimulator or the like).

The antenna 806 is shown in more detail in FIG. 8(*b*). The antenna 806 can be manufactured using any suitable materials using any appropriate manufacturing technology. For example, the antenna 806 may be formed by laser cutting or stamping and may be fabricated from a suitable metals, such as titanium, copper or platinum iridium, commonly used in medical implants. In a particularly advantageous example, the antenna is formed by laser direct structuring of an appropriate antenna material in a dielectric member in the header portion 802(*a*).

The antenna 806 comprises a dipole-loop pair with a gap capacitance which lowers the resonant frequency of the loop and thereby allows the size of the antenna 806 to be reduced. The antenna 806 is configured, by virtue of the gap capacitance, for dual band operation in the MICS Band (402 to 405 MHz) or the Bluetooth band (in the 2400 to 2480 MHz band) and comprises a compound antenna having a magnetic field radiator portion 810 and an electric field radiator portion 814.

The magnetic field radiator portion 810 is the transverse electric (TE) component of the compound antenna 806 and is formed by a conducting member forming a 'loop' that is generally rectangular in shape. The loop 810 has two distinct parts, 810(*a*) and 810(*b*), arranged with an appropriately dimensioned gap 812 therebetween to provide a desired value for the gap capacitance.

One part of the loop 810(*a*) generally adjacent the capacitive gap has a length that is appropriately chosen such that the input impedance of the loop matches the impedance of the radio chipset enabling maximum power transfer at a chosen resonant frequency. This part of the loop 810(*a*) is configured such that the first and second parts of the loop are appropriately located to minimize the phase difference between the electric field and the magnetic field that is generated by the antenna. Further, this part of the loop 810(*a*) is coupled the other part of the loop such that the first and second parts of the loop are appropriately located to generate multiple modes of transverse electric and transverse magnetic leaky waves such that the overall efficiency of the antenna is enhanced.

The first part 810(*a*) of the magnetic field radiator portion 810 is formed at a ground end of the loop 810, whilst the second part 810(b) of the magnetic field radiator portion 810 is formed at a ground end of the loop 810. Thus, the end of the magnetic field radiator portion 810 at the end of the second part 810(b) provides a feed point that is typically connected to a feed pin, or the like. The other end of the magnetic field radiator portion 810 (at the end of the first part 810(a)) provides a ground connection that is connected to a ground point. The magnetic field radiator portion 810 has a shape configured to generate a transverse electric leaky wave in a frequency of interest, in the lossy body tissue of the implant patient, as the current flows from the feed pin to the ground point. The ground connection may be provided via a pin connected to a ground potential on a circuit board inside the housing, or the entire housing could form the ground plane.

The electric field radiator 814 is the transverse magnetic (TM) component of the compound antenna 806 and is formed by a curved or meandered conducting member that is and located internally to the loop 810. The electric field radiator 814 is coupled to the loop portion 810 at a connection point $(x_i, y_i)$ on the perimeter of the loop that is specifically designed to cause the magnetic current flowing through the loop 810 and incident on the electric field radiator 814 to be reflected with minimum amplitude such that it does not disrupt the magnetic current flowing in the loop 810 thereby resulting in a minimization of the phase difference between the electric and the magnetic fields generated in the lossy body tissue. Thus, the electric field radiator portion 814 is configured to generate a transverse electric and a transverse magnetic leaky wave, in a frequency of interest, in the lossy body tissue of the implant patient, thereby increasing the efficiency of the antenna structure.

The antenna 806 is designed, in accordance with the principles described herein, to provide orthogonality of the of the TE and the TM polarization, to excite leaky wave modes in the fat and skin layer in operation, and to maximise far field gain of the transmitter 802 in either of the two bands of operation. Specifically, the antenna 802 has a geometry in which connection point $(x_i, y_i)$ of the electric field radiator 814 along the perimeter of the loop portion 810 and the length of the electric field radiator 808 is configured to tune the antenna to provide the desired orthogonality, leaky wave modes and far field gain.

Design Methodology

Figure 9:
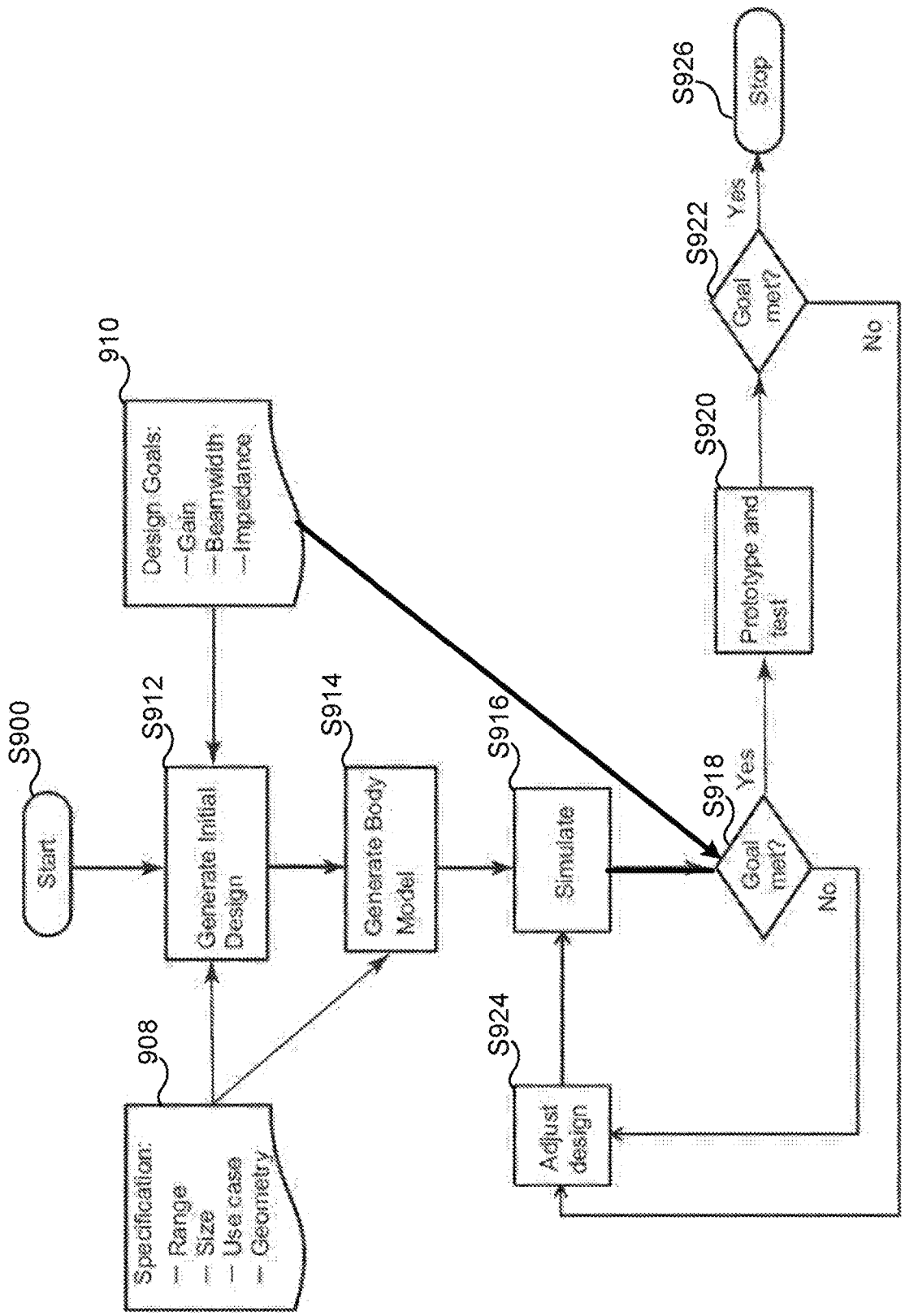
FIG. 9 is a flow diagram showing a procedure that may be used to design an antenna such as the antennas of the implants shown in FIGS. 7 and 8.

FIG. 9 is a flow diagram showing, by way of example only, one possible procedure that may be used to design an antenna such as the antennas described with reference to FIGS. 7 and 8.

After the process starts, at S900, a preliminary antenna design is generated at S912, based on a design specification 908 taking account of one or more design goals 910.

The design specification 908 specifies, for example, one or more of the following: the required range of the implant; the size constraints on the implant antenna; the use case for the implant for which the antenna is being designed; any geometric constraints on the implant antenna; a tissue type at implant location; the size of the implant header; any additional metal structures such as a lead assembly that maybe present in the implant header; header material properties; approximate lead arrangement following surgery; and the final orientation of the implant in the patient pocket.

The design goals 910 are set based on desired antenna performance requirements which are based on link budget calculations that take into account the use case scenarios, implant power budget and the transceiver radio chip characteristics. Typically, for example, the main antenna design goals are antenna input impedance, antenna field of view or half power beam width, and far field gain.

It will be appreciated that not all of the input specifications (and design goals) may be available at the time of initial design (or they may change following the initial design) of the antenna and the method is not limited to having all the specification parameters and/or goals specified.

The initial antenna geometry may similar to that shown in FIG. 7 or 8 or may be some other appropriate antenna design.

Next, a representative body model for the target patient is generated, at S914, with appropriate electromagnetic properties based on appropriate information from the design specification 908 and any other appropriate information (where available) such as patient gender, weight, body characteristics or the like. It will be appreciated that this may be generated at any appropriate time (before, after or in parallel with the initial antenna design).

The body model and initial design provide inputs to a simulator which simulates, at S916, the performance of the antenna in a body of the type represented by the body model. The simulator, in this example, comprises a high frequency simulator that uses finite element or finite difference methods to calculate amplitude and phase of the electric and magnetic fields vectors on the surface of a sphere of radius $\Delta/2\pi$, where $\lambda$ is the guided wavelength in the tissue of implantation. The antenna input impedance and the far field gain of the antenna are calculated and compared to the design goals, at S918, in the frequency band of interest.

If the design goals are not met at S918, then the geometry of the antenna is altered, at S924, by changing: (1) the connection point (xi, yi) of the electric field radiator (or stub) along the perimeter of the loop and (2) changing the length of the electric field radiator (or stub) $L_i$. This changes the phase B between the electric and magnetic dipole moments and the antenna impedances, $Z_E$ and $Z_H$. The adjusted design is then simulated, at S916, and the simulation results compared with the design goals at S918 as described previously.

The adjusting, simulation and comparison steps are repeated iteratively until the design goals are met.

If the initial design, or when an adjusted design, meets the design goals at S918, then the antenna design meeting the goals is fabricated and tested at S920. The antenna is fabricated using standard metal stamping, laser cutting methods or the like. The materials commonly used for implant antennas is titanium, copper or alloys such as platinum-iridium. The fabricated antenna is placed in the header of the implant assembly in which it is to be used. Once fabricated, the implant assembly is tested in an anechoic chamber where the implant is placed in a body 'phantom' comprising a vat filled with tissue mimicking gels.

At 2.4 GHz-2.5 GHz commonly used tissue mimicking gels include:
For skin: SPEAG HBBL1900-3800V3 $\epsilon_r$=39.2 F/m; $\alpha$=1.8 S/m
For fat: SPEAG LCL 2450 V1 $\epsilon_r$=5 F/m; $\alpha$=0.25 S/m
For muscle: SPEAG MBBL1900-3800V3 $\epsilon_r$=52.7 F/m; $\alpha$=1.95 S/m The measured performance parameters of the antenna are compared to the simulated results. If necessary, the antenna design is further adjusted (via steps S924, S916, S918) and modified designs fabricated (at S920) till the measured goals match or exceeds the design goals.

Experimental/Simulation Results

Table 1 below shows the percentages of power that is lost in the various body tissue layers and net radiated power coupled out of the body for the implant antenna described with reference to FIG. 7, and for a standard loop antenna at 2450 MHz.

TABLE 1

Comparison of the radiated power of the compound field antenna design of FIG. 7 to a standard loop antenna having similar dimensions.

| Dissipated power | Loop antenna | Example 1 (FIG. 7) |
|---|---|---|
| in the core Body | 65.19% | 61.43% |
| in the fat | 34.61% | 31.63% |
| In the skin | 0.14% | 2.73% |
| Radiated power in air | 0.06% | 4.21% |
| Radiated power in/through the body | 100% | 100% |

As seen in Table 1, the implantable compound antenna design results in significantly higher radiated power in the air than the standard loop antenna. It has been found that the radiation efficiency of the compound field antenna is greater than twenty times that of the loop antenna (linear scale).

Figure 10B:
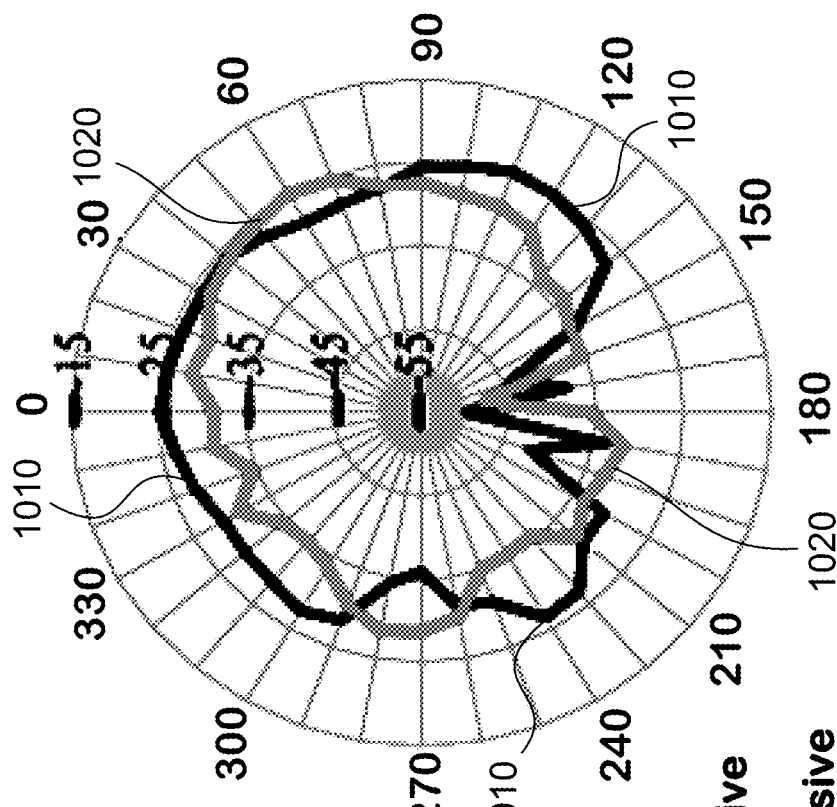
FIGS. 10(a) and 10(b) show measured antenna gain as a function of angle in the elevation plane for a compound antenna.
Figure 10A:
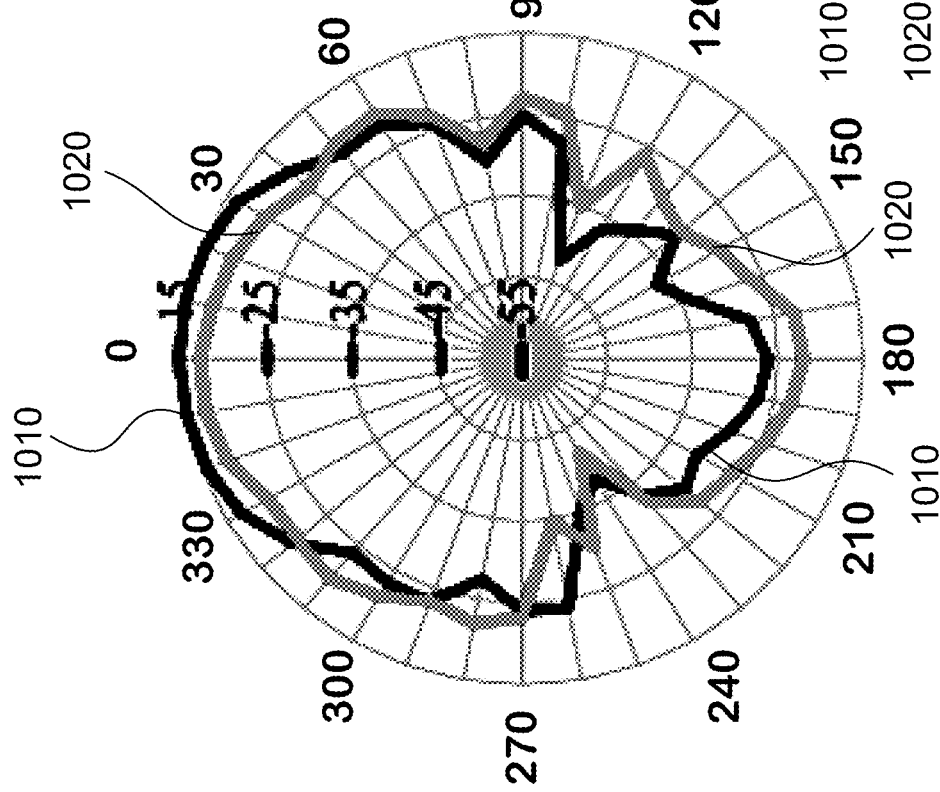

FIGS. 10(a) and 10(b) show measured antenna gain as a function of angle in the elevation plane for a compound antenna. The gain is measured in both the vertical (FIG. 10(a)) and horizontal (FIG. 10(b)) polarizations relative to the gravity vector. In FIG. 10, the two plots shown include a first plot 1010 representing active measurements, done using a CSR1010 Bluetooth SMART™ chipset, and a second plot 1020 representing passive measurements, done using a network analyzer. The receive antenna is a standard gain horn resonant in the 2300 MHz to 2500 MHz band. For the active measurement the receiver is a spectrum analyzer that measures peak received power in dBm. The plots clearly show that the antenna is linearly polarized in the vertical direction (along the gravity vector).

Figure 11:
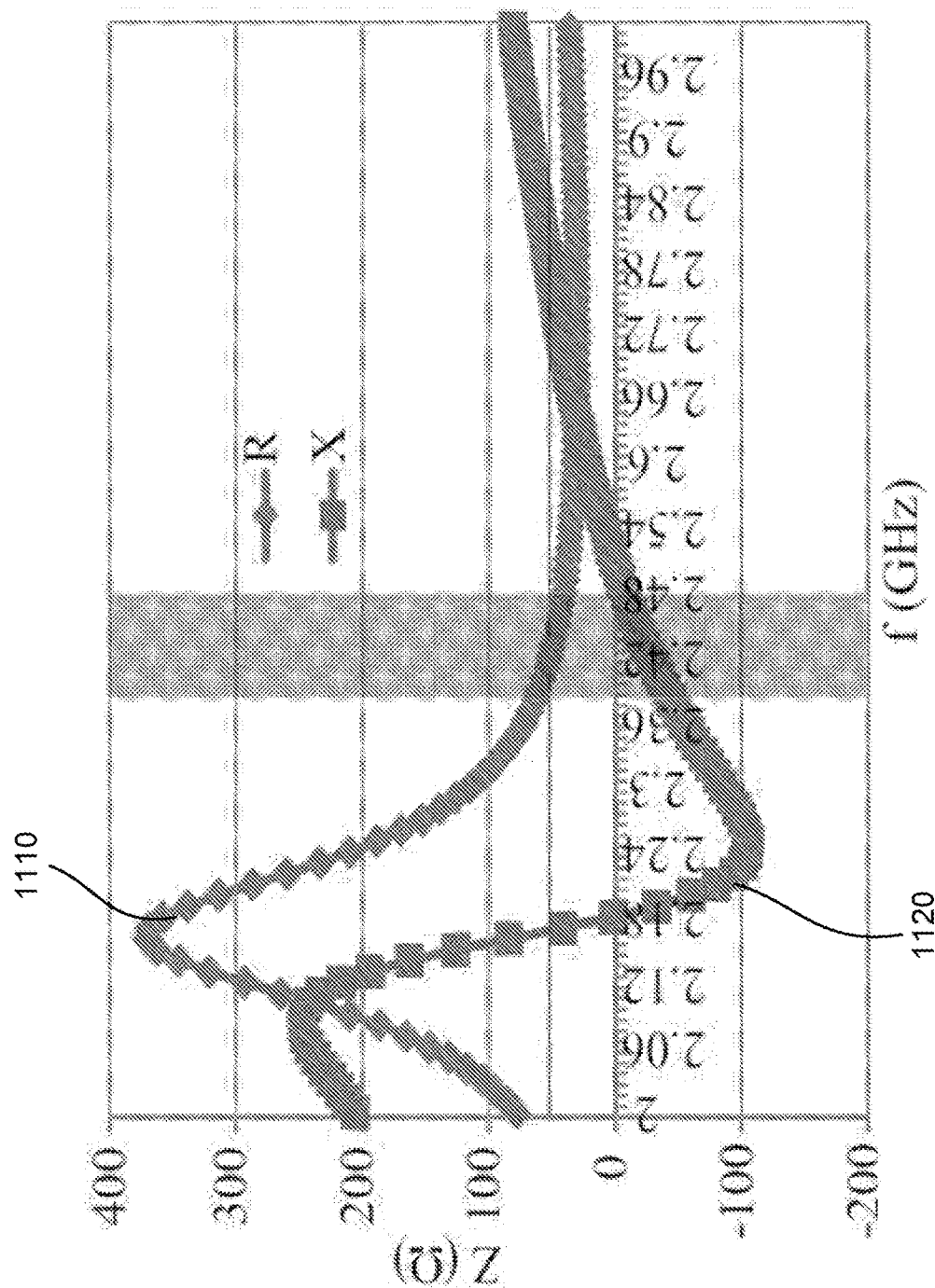
FIG. 11 shows the real and imaginary parts of an input impedance of an antenna as a function of frequency.

FIG. 11 shows the real 1110 and imaginary 1120 parts of the input impedance of the antenna as a function of frequency.

Figure 12:
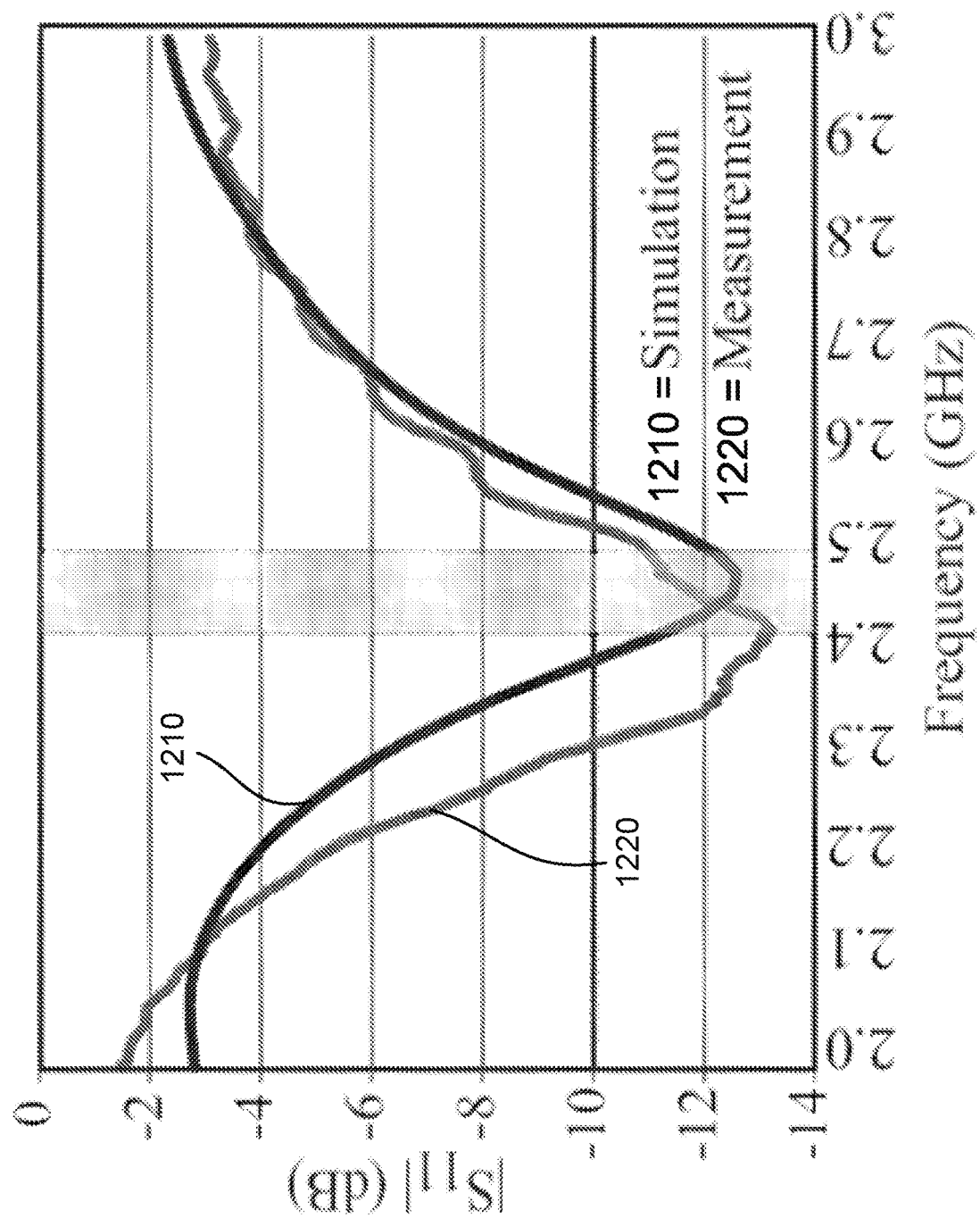
FIG. 12 shows the simulated and measured return loss of an antenna as a function of frequency.

FIG. 12 shows the simulated 1210 and measured 1220 return loss of the antenna as a function of frequency. The return loss indicates how well an antenna's impedance is matched to the transmitter's impedance. In the example shown the common transmitter impedance is 50Ω.

Modifications and Alternatives

Detailed embodiments have been described above. As those skilled in the art will appreciate, a number of modifications and alternatives can be made to the above embodiments whilst still benefiting from the inventions embodied therein.

It will be appreciated, for example, that other shapes of the antenna may be used in dependence on requirements of the application in which the antenna is employed.

Various other modifications will be apparent to those skilled in the art and will not be described in further detail here.

REFERENCES

A general background to antenna design and the technology discussed herein can be found in the following documents:

[1] Kiourti. A., K. A. Psathas, K. S. Nikita, Implantable and Ingestible Medical Devices with Wireless Telemetry Functionalities: A Review of Current Status and Challenges, Wiley Bioelectromagnetics, vol. 35, issue 1, pp. 1-15, January 2014.

[2] Li et al., Inverted e antenna with capacitance loading for use with an implantable medical device, U.S. patent application Ser. No. 13/538,501, 2012, published as U.S. 2014/0002314 (2014).

[3] Mashiach, A. and Mueller, C., Antenna providing variable communication with an implant, CA Patent App. CA 2,850,445, 2013.

[4] Amundson, M. D. and Von Arx, J. A. and Linder, W. J. and Rawat, P. and Mass, W. R., Circumferential antenna for an implantable medical device, U.S. Pat. No. 6,614,406, 2003.

[5] Renken, G. W., Implant device telemetry antenna, U.S. Pat. No. 6,009,350, 1999.

[6] D. M. Grimes and C. A. Grimes, Minimum Q of electrically small antennas: a critical review, Microwave Optical Tech. Lett., vol. 28, pp. 172-177, February 2001.

[7] M. J. Underhill and M. J. Blewett, Unidirectional tuned loop antennas using combined loop and dipole modes, in Proc. Inst. Elect. Eng. 8th Int. Conf. HF Radio Systems and Techniques, July 2000, Pub. 474, pp. 37-41.

[8] D. H. Kwon, On the Radiation Q and the Gain of Crossed Electric and Magnetic Dipole Moments, IEEE Transactions on Antennas and Propagation, Vol. 53, No. 5, May 2005.

[9] D. M. Pozar, New results for minimum Q, maximum gain, and polarization properties of electrically small arbitrary antennas, 3rd European Conference on Antennas and Propagation, pp. 1993, 23-27 Mar. 2009.

[10] McLean, J. S., P×M antenna with improved radiation characteristics over a broad frequency range, U.S. Pat. No. 7,388,550, 2008.

[11] Grimes, C. A., Grimes, D. M., Tefiku, F. and Lui, G., Electrically-small low Q radiator structure and method of producing EM waves therewith, U.S. Pat. No. 6,437,750, 2002.

[12] Brown, F. J., Planar compound loop antenna, U.S. Pat. No. 8,144,065, 2012.

[13] Orsi et. al., Capacitively coupled compound loop antenna, US 20130113666, May 9, 2013.

[14] S. O. Driscoll, A. S. Y. Poon, T. H. Meng, Wireless power transmission for implantable medical devices, U.S. Pat. No. 8,634,928 B1, Jan. 21, 2014.

[15] A. S. Y. Poon, Electromagnetic field focusing for short-range wireless power transmission, Proc. IEEE Radio and Wireless Symposium (RWS), Santa Clara, Calif., January 2012.

[16] Ho, J. S., A. J. Yeh, E. Neofytou, S. Kim, Y. Tanabe, B. Patlolla, R. E. Beygui, and A. S. Y. Poon, Wireless power transfer to deep-tissue microimplants, PNAS, 111, 7974-7979 (2014).

[17] S. Gabriel, R. W. Lau, and C. Gabriel, The Dielectric Properties of Biological Tissues: III. Parametric models for the Dielectric Spectrum of Tissues, Phys. Med. Bio., vol. 41, pp. 227193, November 1996.

[18] Orfanidis, S. J., Electromagnetic waves and antennas, Online Publication, 21 Jun. 2004

[19] Karlsson, A., Physical limitations of antennas in a lossy medium, IEEE Trans. on Antennas and Propagation, Vol. 52, pp. 2027-2033, 2004.

[20] R. W. P. King and G. S. Smith, Antennas in Matter, Cambridge, London, U.K.: MIT Press, 1981.

[21] Harrington, R. F., Time Harmonic Electromagnetic Fields. New York: McGraw-Hill, 1961.
[22] G. Lovat, P. Burghignoli, and D. R. Jackson, Fundamental properties and optimization of broadside radiation from uniform leaky-wave antennas, IEEE Trans. Antennas Propagat, vol. 54, no. 5, pp. 14421452, May 2006.
[23] A. Ip, and D. R. Jackson, Radiation from cylindrical leaky waves, IEEE Trans. Antennas Propagat., vol. 38, no. 4, pp. 482488, April 1990.
[24] Kim, K. Y., Guided and leaky modes for circular open electromagnetic waveguides: Dielectric, plasma and metamaterial column, Ph.D. Thesis, December 2004.
[25] Hanson, G. W. and A. B. Yakovlev, An analysis of leaky wave dispersion phenomena in the vicinity of cutoff using complex frequency plane singularities, Radio Science, Vol. 33, No. 4, 803-819, 1998.
[26] T. Needham, Visual Complex Analysis, Oxford University Press, 1999.
[27] Schantz, H. G., Near Field Phase Behaviour, In proceeding of: Antennas and Propagation Society International Symposium, 2005 IEEE, Volume: 3B.
[28] also cited as [8] Kwon, D. H., On the radiation Q and the gain of crossed electric and magnetic dipole moments, Antennas and Propagation, IEEE Transactions on, vol. 53, no. 5, pp. 1681, 1687, May 2005.

The invention claimed is:

1. An antenna for transmitting signals from a transmitter to a corresponding receiver even when there is signal attenuating human body tissue of a user positioned in a signal path between the transmitter and the corresponding receiver, the antenna comprising:
a magnetic field radiator portion and an electric field radiator portion;
wherein the magnetic field radiator portion and electric field radiator portion are arranged relative to one another such that, when said signal attenuating human body tissue of the user is located between the transmitter and the corresponding receiver, the antenna generates at least one of a transverse electric leaky wave or a transverse magnetic leaky wave in body tissue of the user such that the body tissue, in which the at least one transverse electric leaky wave or a transverse magnetic leaky wave is generated, acts as a waveguide for said at least one of a transverse electric leaky wave or a transverse magnetic leaky wave, and such that at least one of the radiation efficiency of the antenna or the far field gain of the antenna is maximized.

2. An antenna according to claim 1, wherein the antenna is configured to operate with a transmitter of a device, when the device is located in a pocket of body tissue of said user, in which the signal attenuating human body tissue is located in a first direction relative to the transmitter, and the body tissue in which the at least one transverse electric leaky wave or a transverse magnetic leaky wave is generated extends in a second direction, relative to the transmitter, the second direction being different than the first direction.

3. An antenna according to claim 1, wherein the magnetic field radiator portion and electric field radiator portion are arranged for the generation of at least one surface wave, the at least one surface wave propagating on body tissue comprising a skin layer, whereby the skin layer acts as a waveguide for propagating signals from said transmitter to said receiver.

4. An antenna according to claim 3, wherein the magnetic field radiator portion and electric field radiator portion are arranged for the generation of at least one surface wave mode, the at least one surface wave minimizing propagation loss between the transmitter and the corresponding receiver.

5. The antenna as recited in claim 1, wherein the magnetic field radiator portion comprises a loop, formed by a first conducting member having a first end and a second end, and having a feed pin at the first end and a ground point at the second end, and wherein the magnetic field radiator portion is configured to generate a magnetic field in the frequency of operation as current flows from the feed pin to the ground point.

6. The antenna as recited in claim 1, wherein the antenna is configured to generate a transverse electric leaky wave in a frequency of operation in said human body tissue.

7. The antenna as recited in claim 1, wherein the magnetic field radiator portion comprises a loop and wherein said electric field radiator is connected to said magnetic field radiator at a location, the location being predetermined to be a location resulting in said generation of at least one of a transverse electric leaky wave or a transverse magnetic leaky wave.

8. The antenna as recited in claim 1, wherein the magnetic field radiator portion comprises a loop and wherein said electric field radiator is connected to said magnetic field radiator at a specific location on a perimeter of the loop to minimize current reflected back into the loop and disrupting magnetic current flowing through the loop, to reduce a phase difference between electric and magnetic fields generated in the body tissue.

9. The antenna as recited in claim 1, wherein the magnetic field radiator portion comprises a loop and wherein the magnetic loop comprises a capacitive gap configured to reduce a resonant frequency of the loop.

10. The compound field antenna as recited in claim 9, wherein the antenna is configured to operate with a radio chipset, wherein a conducting member extends proximate the capacitive gap, and wherein the conducting member has a length configured such that an input impedance of said loop matches an impedance of the radio chipset.

11. The antenna as recited in claim 1 configured such that, in operation when there is signal attenuating human body tissue of a user positioned in the signal path between the transmitter and the corresponding receiver, the body tissue in which the at least one transverse electric leaky wave or transverse magnetic leaky wave is generated enhances the far field radiation efficiency of the antenna.

12. The antenna as recited in claim 1 configured such that, in operation when there is signal attenuating human body tissue of a user positioned in the signal path between the transmitter and the corresponding receiver, the body tissue in which the at least one transverse electric leaky wave or transverse magnetic leaky wave is generated enlarges an effective aperture of the antenna.

13. A device comprising a transmitter provided with an antenna as claimed in claim 1.

14. A device comprising a transmitter for transmitting signals to a corresponding receiver even when there is signal attenuating human body tissue positioned in a signal path between the transmitter and the corresponding receiver, wherein the transmitter comprising an antenna having a magnetic field radiator portion and an electric field radiator portion, wherein the magnetic field radiator portion and electric field radiator portion are arranged relative to one another such that, when said signal attenuating human body tissue of the user is located between the transmitter and the corresponding receiver, the antenna generates at least one of a transverse electric leaky wave or a transverse magnetic leaky wave in body tissue of the user such that the body tissue, in which the at least one transverse electric leaky wave or a transverse magnetic leaky wave is generated, acts as a waveguide for said at least one of a transverse electric leaky wave or a transverse magnetic leaky wave, and such that at least one of the radiation efficiency of the antenna or the far field gain of the antenna is maximized.

\* \* \* \* \*